US012310936B2

(12) United States Patent
Björnstedt et al.

(10) Patent No.: US 12,310,936 B2
(45) Date of Patent: May 27, 2025

(54) PHARMACEUTICAL COMPOSITIONS FOR THE TREATMENT OF CANCER

(71) Applicant: Seleq Oy, Turku (FI)

(72) Inventors: Mikael Björnstedt, Huddinge (SE); Adnane Achour, Stockholm (SE); Hugh Salter, Sollentuna (SE); Tatiana Sandalova, Sollentuna (SE)

(73) Assignee: Seleq Oy, Turku (FI)

( * ) Notice: Subject to any disclaimer, the term of this patent is extended or adjusted under 35 U.S.C. 154(b) by 1043 days.

(21) Appl. No.: 17/055,182

(22) PCT Filed: May 21, 2019

(86) PCT No.: PCT/FI2019/050391
§ 371 (c)(1),
(2) Date: Nov. 13, 2020

(87) PCT Pub. No.: WO2019/224428
PCT Pub. Date: Nov. 28, 2019

(65) Prior Publication Data
US 2021/0220310 A1    Jul. 22, 2021

(30) Foreign Application Priority Data

May 22, 2018  (FI) ...................................... 20185470

(51) Int. Cl.
| | | |
|---|---|---|
| A61K 31/198 | (2006.01) | |
| A61K 9/127 | (2025.01) | |
| A61K 9/51 | (2006.01) | |
| A61K 31/192 | (2006.01) | |
| A61K 31/405 | (2006.01) | |
| A61K 38/45 | (2006.01) | |
| A61K 48/00 | (2006.01) | |
| A61P 35/00 | (2006.01) | |

(52) U.S. Cl.
CPC ............ *A61K 31/198* (2013.01); *A61K 9/127* (2013.01); *A61K 9/51* (2013.01); *A61K 31/192* (2013.01); *A61K 31/405* (2013.01); *A61K 38/45* (2013.01); *A61K 48/0058* (2013.01); *A61K 48/0066* (2013.01); *A61P 35/00* (2018.01)

(58) Field of Classification Search
CPC ........ A61K 31/198; A61K 9/127; A61K 9/51; A61K 31/192; A61K 31/405; A61K 38/45; A61K 48/0058; A61K 48/0066; A61K 33/04; A61K 31/00; A61P 35/00
See application file for complete search history.

(56) References Cited

U.S. PATENT DOCUMENTS

| | | | | |
|---|---|---|---|---|
| 6,656,509 B1 * | 12/2003 | Stiefel | .................... | A61P 35/00 |
| | | | | 424/617 |
| 2003/0083383 A1 * | 5/2003 | Spallholz | .............. | A23L 33/175 |
| | | | | 514/561 |

FOREIGN PATENT DOCUMENTS

| | | | |
|---|---|---|---|
| EP | 1652519 A1 | 5/2006 | |
| WO | WO-2019070750 A1 * | 4/2019 | ........... A61K 31/198 |

OTHER PUBLICATIONS

Mutation Research 11-80 481 (2001) 219 229 (Year: 2001).*
Bhattacharya et al. "Tumor Vascular Maturation and Improved Drug Delivery Induced by Methylselenocysteine Leads to therapeutic Synergy with Anticancer Drugs" Clin Cancer Res., vol. 14, No. 12, XP002792923, Jun. 15, 2008, 8 Pages.
Bhattacharya, A. "Methylselenocysteine—a promising antiangiogenic agent for overcoming drug delivery barriers in solid malignancies for therapeautic synergy with anticancer drugs" In: Expert Opinion. Drug Deliv, vol. 8, No. 6, DOI: 10.1517/17425247.2011.571672, Jun. 30, 2011, 15 Pages.
Finnish Patent and Registration Office, Search Report, Application No. 20185470, Mailed Dec. 20, 2018, 2 Pages.
Notification of Transmittal of The International Search Report and The Written Opinion of The International Searching Authority, or the Declaration, Application No. PCT/FI2019/050391, Mailed Jul. 31, 2019, 12 Pages.
Pinto et al. "Selective Transamination of methyselenocysteine and selenomethionine, respectively, by glutamine transaminase (GT) K and L" In: Annual Meeting of the federation of American Societies for Experimental Biology, Apr. 22, 2013, 2 Pages.
Wang, Z. "A study on Se-methylselenocysteine inducing hepatocellular carcinoma cell apoptosis and its mechanism" Jiangsu Med J.vol. 38, No. 11, Jun. 2012, 6 Pages.

* cited by examiner

*Primary Examiner* — Snigdha Maewall
(74) *Attorney, Agent, or Firm* — Ziegler IP Law Group, LLC.

(57) ABSTRACT

A chemotherapeutically active pharmaceutical composition includes at least one pharmaceutically acceptable seleno amino acid derivative compound for use in the treatment of liver or pancreas cancer, wherein the chemotherapeutically active pharmaceutical composition is used in combination with an agent capable of increasing cytotoxicity of the seleno amino acid derivative compound.

14 Claims, 1 Drawing Sheet
Specification includes a Sequence Listing.

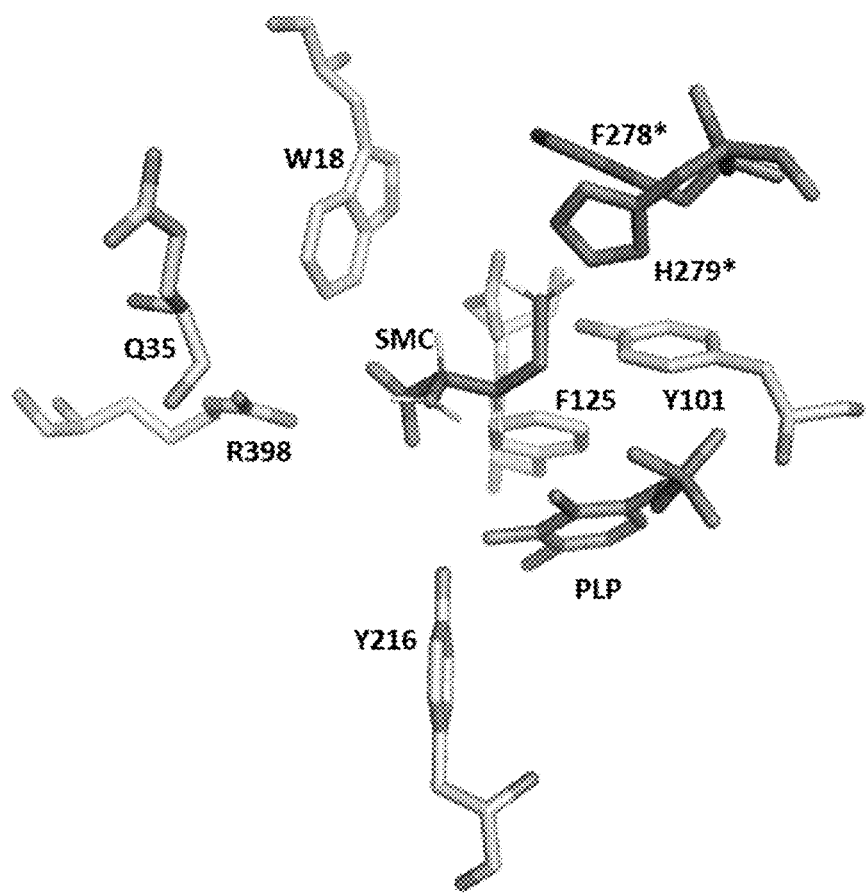

SEQUENCE LISTING

```
<160> NUMBER OF SEQ ID NOS: 3

<210> SEQ ID NO 1
<211> LENGTH: 422
<212> TYPE: PRT
<213> ORGANISM: Homo sapiens

<400> SEQUENCE: 1

Met Ala Lys Gln Leu Gln Ala Arg Arg Leu Asp Gly Ile Asp Tyr Asn
1               5                   10                  15

Pro Trp Val Glu Phe Val Lys Leu Ala Ser Glu His Asp Val Val Asn
            20                  25                  30

Leu Gly Gln Gly Phe Pro Asp Phe Pro Pro Asp Phe Ala Val Glu
        35                  40                  45

Ala Phe Gln His Ala Val Ser Gly Asp Phe Met Leu Asn Gln Tyr Thr
    50                  55                  60

Lys Thr Phe Gly Tyr Pro Pro Leu Thr Lys Ile Leu Ala Ser Phe Phe
65                  70                  75                  80

Gly Glu Leu Leu Gly Gln Glu Ile Asp Pro Leu Arg Asn Val Leu Val
                85                  90                  95

Thr Val Gly Gly Tyr Gly Ala Leu Phe Thr Ala Phe Gln Ala Leu Val
            100                 105                 110

Asp Glu Gly Asp Glu Val Ile Ile Ile Glu Pro Phe Phe Asp Cys Tyr
        115                 120                 125

Glu Pro Met Thr Met Met Ala Gly Gly Arg Pro Val Phe Val Ser Leu
130                 135                 140

Lys Pro Gly Pro Ile Gln Asn Gly Glu Leu Gly Ser Ser Ser Asn Trp
145                 150                 155                 160

Gln Leu Asp Pro Met Glu Leu Ala Gly Lys Phe Thr Ser Arg Thr Lys
                165                 170                 175

Ala Leu Val Leu Asn Thr Pro Asn Asn Pro Leu Gly Lys Val Phe Ser
            180                 185                 190

Arg Glu Glu Leu Glu Leu Val Ala Ser Leu Cys Gln Gln His Asp Val
        195                 200                 205

Val Cys Ile Thr Asp Glu Val Tyr Gln Trp Met Val Tyr Asp Gly His
    210                 215                 220

Gln His Ile Ser Ile Ala Ser Leu Pro Gly Met Trp Glu Arg Thr Leu
225                 230                 235                 240

Thr Ile Gly Ser Ala Gly Lys Thr Phe Ser Ala Thr Gly Trp Lys Val
                245                 250                 255
```

```
Gly Trp Val Leu Gly Pro Asp His Ile Met Lys His Leu Arg Thr Val
            260                 265                 270

His Gln Asn Ser Val Phe His Cys Pro Thr Gln Ser Gln Ala Ala Val
        275                 280                 285

Ala Glu Ser Phe Glu Arg Glu Gln Leu Leu Phe Arg Gln Pro Ser Ser
    290                 295                 300

Tyr Phe Val Gln Phe Pro Gln Ala Met Gln Arg Cys Arg Asp His Met
305                 310                 315                 320

Ile Arg Ser Leu Gln Ser Val Gly Leu Lys Pro Ile Ile Pro Gln Gly
                325                 330                 335

Ser Tyr Phe Leu Ile Thr Asp Ile Ser Asp Phe Lys Arg Lys Met Pro
            340                 345                 350

Asp Leu Pro Gly Ala Val Asp Glu Pro Tyr Asp Arg Arg Phe Val Lys
        355                 360                 365

Trp Met Ile Lys Asn Lys Gly Leu Val Ala Ile Pro Val Ser Ile Phe
    370                 375                 380

Tyr Ser Val Pro His Gln Lys His Phe Asp His Tyr Ile Arg Phe Cys
385                 390                 395                 400

Phe Val Lys Asp Glu Ala Thr Leu Gln Ala Met Asp Glu Lys Leu Arg
                405                 410                 415

Lys Trp Lys Val Glu Leu
            420

<210> SEQ ID NO 2
<211> LENGTH: 422
<212> TYPE: PRT
<213> ORGANISM: Homo sapiens

<400> SEQUENCE: 2

Met Ala Lys Gln Leu Gln Ala Arg Arg Leu Asp Gly Ile Asp Tyr Asn
1               5                   10                  15

Pro Trp Val Glu Phe Val Lys Leu Ala Ser Glu His Asp Val Val Asn
                20                  25                  30

Leu Gly Gln Gly Phe Pro Asp Phe Pro Pro Asp Phe Ala Val Glu
            35                  40                  45

Ala Phe Gln His Ala Val Ser Gly Asp Phe Met Leu Asn Gln Tyr Thr
    50                  55                  60

Lys Thr Phe Gly Tyr Pro Pro Leu Thr Lys Ile Leu Ala Ser Phe Phe
65                  70                  75                  80

Gly Glu Leu Leu Gly Gln Glu Ile Asp Pro Leu Arg Asn Val Leu Val
                85                  90                  95

Thr Val Gly Gly His Gly Ala Leu Phe Thr Ala Phe Gln Ala Leu Val
            100                 105                 110

Asp Glu Gly Asp Glu Val Ile Ile Ile Glu Pro Phe Phe Asp Cys Tyr
        115                 120                 125

Glu Pro Met Thr Met Met Ala Gly Gly Arg Pro Val Phe Val Ser Leu
    130                 135                 140

Lys Pro Gly Pro Ile Gln Asn Gly Glu Leu Gly Ser Ser Ser Asn Trp
145                 150                 155                 160

Gln Leu Asp Pro Met Glu Leu Ala Gly Lys Phe Thr Ser Arg Thr Lys
                165                 170                 175

Ala Leu Val Leu Asn Thr Pro Asn Asn Pro Leu Gly Lys Val Phe Ser
            180                 185                 190

Arg Glu Glu Leu Glu Leu Val Ala Ser Leu Cys Gln Gln His Asp Val
        195                 200                 205
```

```
Val Cys Ile Thr Asp Glu Val Tyr Gln Trp Met Val Tyr Asp Gly His
    210                 215                 220
Gln His Ile Ser Ile Ala Ser Leu Pro Gly Met Trp Glu Arg Thr Leu
225                 230                 235                 240
Thr Ile Gly Ser Ala Gly Lys Thr Phe Ser Ala Thr Gly Trp Lys Val
            245                 250                 255
Gly Trp Val Leu Gly Pro Asp His Ile Met Lys His Leu Arg Thr Val
                260                 265                 270
His Gln Asn Ser Val Phe His Cys Pro Thr Gln Ser Gln Ala Ala Val
        275                 280                 285
Ala Glu Ser Phe Glu Arg Glu Gln Leu Leu Phe Arg Gln Pro Ser Ser
    290                 295                 300
Tyr Phe Val Gln Phe Pro Gln Ala Met Gln Arg Cys Arg Asp His Met
305                 310                 315                 320
Ile Arg Ser Leu Gln Ser Val Gly Leu Lys Pro Ile Ile Pro Gln Gly
            325                 330                 335
Ser Tyr Phe Leu Ile Thr Asp Ile Ser Asp Phe Lys Arg Lys Met Pro
                340                 345                 350
Asp Leu Pro Gly Ala Val Asp Glu Pro Tyr Arg Arg Phe Val Lys
        355                 360                 365
Trp Met Ile Lys Asn Lys Gly Leu Val Ala Ile Pro Val Ser Ile Phe
    370                 375                 380
Tyr Ser Val Pro His Gln Lys His Phe Asp His Tyr Ile Arg Phe Cys
385                 390                 395                 400
Phe Val Lys Asp Glu Ala Thr Leu Gln Ala Met Asp Glu Lys Leu Arg
            405                 410                 415
Lys Trp Lys Val Glu Leu
        420

<210> SEQ ID NO 3
<211> LENGTH: 422
<212> TYPE: PRT
<213> ORGANISM: Homo sapiens

<400> SEQUENCE: 3

Met Ala Lys Gln Leu Gln Ala Arg Arg Leu Asp Gly Ile Asp Tyr Asn
1               5                   10                  15
Pro Trp Val Glu Phe Val Lys Leu Ala Ser Glu His Asp Val Val Asn
            20                  25                  30
Leu Gly Gln Gly Phe Pro Asp Phe Pro Pro Asp Phe Ala Val Glu
        35                  40                  45
Ala Phe Gln His Ala Val Ser Gly Asp Phe Met Leu Asn Gln Tyr Thr
    50                  55                  60
Lys Thr Phe Gly Tyr Pro Pro Leu Thr Lys Ile Leu Ala Ser Phe Phe
65                  70                  75                  80
Gly Glu Leu Leu Gly Gln Glu Ile Asp Pro Leu Arg Asn Val Leu Val
            85                  90                  95
Thr Val Gly Gly Tyr Gly Ala Leu Phe Thr Ala Phe Gln Ala Leu Val
                100                 105                 110
Asp Glu Gly Asp Glu Val Ile Ile Ile Glu Pro Phe Phe Asp Cys Tyr
        115                 120                 125
Glu Pro Met Thr Met Met Ala Gly Gly Arg Pro Val Phe Val Ser Leu
    130                 135                 140
Lys Pro Gly Pro Ile Gln Asn Gly Glu Leu Gly Ser Ser Ser Asn Trp
```

-continued

```
            145                 150                 155                 160
        Gln Leu Asp Pro Met Glu Leu Ala Gly Lys Phe Thr Ser Arg Thr Lys
                        165                 170                 175

Ala Leu Val Leu Asn Thr Pro Asn Asn Pro Leu Gly Lys Val Phe Ser
                        180                 185                 190

Arg Glu Glu Leu Glu Leu Val Ala Ser Leu Cys Gln Gln His Asp Val
                    195                 200                 205

Val Cys Ile Thr Asp Glu Val Tyr Gln Trp Met Val Tyr Asp Gly His
                210                 215                 220

Gln His Ile Ser Ile Ala Ser Leu Pro Gly Met Trp Glu Arg Thr Leu
        225                 230                 235                 240

Thr Ile Gly Ser Ala Gly Lys Thr Phe Ser Ala Thr Gly Trp Lys Val
                        245                 250                 255

Gly Trp Val Leu Gly Pro Asp His Ile Met Lys His Leu Arg Thr Val
                        260                 265                 270

His Gln Asn Ser Val Phe Phe Cys Pro Thr Gln Ser Gln Ala Ala Val
                        275                 280                 285

Ala Glu Ser Phe Glu Arg Glu Gln Leu Leu Phe Arg Gln Pro Ser Ser
                290                 295                 300

Tyr Phe Val Gln Phe Pro Gln Ala Met Gln Arg Cys Arg Asp His Met
        305                 310                 315                 320

Ile Arg Ser Leu Gln Ser Val Gly Leu Lys Pro Ile Ile Pro Gln Gly
                        325                 330                 335

Ser Tyr Phe Leu Ile Thr Asp Ile Ser Asp Phe Lys Arg Lys Met Pro
                        340                 345                 350

Asp Leu Pro Gly Ala Val Asp Glu Pro Tyr Asp Arg Arg Phe Val Lys
                    355                 360                 365

Trp Met Ile Lys Asn Lys Gly Leu Val Ala Ile Pro Val Ser Ile Phe
                    370                 375                 380

Tyr Ser Val Pro His Gln Lys His Phe Asp His Tyr Ile Arg Phe Cys
        385                 390                 395                 400

Phe Val Lys Asp Glu Ala Thr Leu Gln Ala Met Asp Glu Lys Leu Arg
                        405                 410                 415

Lys Trp Lys Val Glu Leu
                        420
```

PHARMACEUTICAL COMPOSITIONS FOR THE TREATMENT OF CANCER

TECHNICAL FIELD

The present disclosure relates generally to pharmaceutical compositions for use in the treatment of cancer, more specifically, to chemotherapeutically active pharmaceutical compositions for inhibiting growth of cancer cells of the liver or pancreas. Moreover, the present disclosure relates to a method for inhibiting growth of cancer cells of the liver or pancreas.

BACKGROUND

Hepatocellular carcinoma (HCC) is a primary malignancy of the liver. It is now a third leading cause of cancer deaths worldwide, affecting over 500,000 people. The incidence of HCC is increasing as larger numbers of patients are diagnosed with cirrhosis secondary to alcohol and/or viral hepatitis and genetic disorders. Other causes for HCC are related to further life style factors such as fatty liver disease and obesity, which cause cirrhosis and liver cancer. Most of the conventionally known medications, such as local ablative therapies, including radiofrequency ablation, chemoembolization, and chemotherapeutic agents, may prolong life but are not curative.

The prompt and accurate initiation of drug dosages to a patient is essential in the treatment of primary malignancy of the liver. An inappropriate formulation may produce therapeutic failure as the result of sub-therapeutic drug levels or, alternatively, due to toxic drug levels (overdose). Conventionally, the multikinase inhibitor sorafenib is used as the first systemic treatment which can prolong survival of patients with liver cancer. However, the treatment only yields a survival advantage of less than three months. Moreover, sorafenib is not curative and the treatment is life-long. Further, a majority of patients experience side effects, such as hand-foot syndrome, diarrhoea, nausea, fatigue and so forth, when undergoing treatment with sorafenib. Also, use of conventionally known pharmaceutical compositions is restricted to patients with a normal liver function.

Furthermore, conventional curative options for the treatment of liver cancer are surgical resection or liver transplantation. However, at the time of diagnosis a majority of patients present with advanced tumour growth are not eligible for these treatment options due to vascular invasion and/or distant metastasis. Additionally, surgical resection or liver transplantation is expensive.

Document US 2003/0083383 discloses a method of using synthetic L-Se-methylselenocysteine as a nutraceutical, for preventing or reducing the risk of developing liver cancer. The document does however not discuss treatment of liver cancer with its product. Similarly, document EP 1205471 concerns the same product (synthetic L-Se-methylselenocysteine) and its use for preventing or reducing the risk of developing cancer. Neither document however discusses treatment of cancer.

Therefore, in light of the foregoing discussion, there exists a need to overcome the aforementioned drawbacks associated with existing pharmaceutical composition for treatment of liver and pancreas cancers. Also, there exists a need of improved therapeutically active pharmaceutical compositions for inhibiting growth of cancer cells and for killing such cells.

SUMMARY

The present disclosure seeks to provide chemotherapeutically active pharmaceutical compositions for inhibiting growth of cancer cells of an organ, and even for killing such cells. Inhibition of growth and killing of cancer cells is in this description defined with the general term of treating such cancer cells. Indeed, the present description is concerned with treatment of cancer, not only prevention of cancer. The present disclosure also seeks to provide methods for inhibiting growth/killing of cancer cells of an organ. The present disclosure seeks to provide a solution to the existing problem of low efficacy and side-effects associated with available pharmaceutical compositions for inhibiting growth of cancer cells. An aim of the present disclosure is to provide a solution that overcomes at least partially the problems encountered in prior art and provides a chemotherapeutically active pharmaceutical composition having high anti-tumour efficacy and minimal side-effects.

In one aspect, the disclosed embodiment relates to a chemotherapeutically active pharmaceutical composition comprising at least one pharmaceutically acceptable seleno amino acid derivative compound for use in the treatment of liver or pancreas cancer, wherein said chemotherapeutically active pharmaceutical composition is used in combination with an agent capable of increasing cytotoxicity of the seleno amino acid derivative compound.

The present disclosure also provides a method for treating liver or pancreas cancer, comprising administration of:
  a) a chemotherapeutically active pharmaceutical composition comprising at least one pharmaceutically acceptable seleno amino acid derivative compound, and
  b) an agent capable of increasing cytotoxicity of the seleno amino acid derivative compound.

The method includes orally administering to a subject an effective amount of the above-defined pharmaceutical composition in per day doses.

Embodiments of the present disclosure substantially eliminate or at least partially address the aforementioned problems in the prior art and enable a medical team to determine an effective personalised drug dose for patients undergoing treatment of liver or pancreas malignancy.

Additional aspects, advantages, features and objects of the present disclosure would be made apparent from the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE FIGURE

FIG. 1 shows a model of SMC interaction points with KYAT1.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also unique and possible.

In an aspect, the disclosed embodiment relates to a chemotherapeutically active pharmaceutical composition comprising at least one pharmaceutically acceptable seleno amino acid derivative compound for use in the treatment of liver or pancreas cancer, wherein said chemotherapeutically active pharmaceutical composition is used in combination with an agent capable of increasing cytotoxicity of the seleno amino acid derivative compound. In one embodiment, the intracellular beta-elimination activity of the kynurenine aminotransferase I or kynurenine aminotransferase III enzyme of the cancer cell is at least 1.5 times higher than the intracellular beta-elimination activity of the kynurenine aminotransferase I or kynurenine aminotransferase III enzyme of a non-cancer cell of the organ.

The present disclosure also provides a method for treating liver or pancreas cancer, comprising administration of:
  a) a chemotherapeutically active pharmaceutical composition comprising at least one pharmaceutically acceptable seleno amino acid derivative compound, and
  b) an agent capable of increasing cytotoxicity of the seleno amino acid derivative compound.

In one embodiment, the intracellular beta-elimination activity of the kynurenine aminotransferase I or kynurenine aminotransferase III enzyme of the cancer cell is at least 1.5 times higher than the intracellular beta-elimination activity of the kynurenine aminotransferase I or kynurenine aminotransferase III enzyme of a non-cancer cell of the organ. The method includes orally administering to a subject an effective amount of the above-defined pharmaceutical composition in per day doses.

The present disclosure provides a chemotherapeutically active pharmaceutical composition for treating cancer cells. Moreover, present disclosure provides a method for inhibiting growth of cancer cells of the liver. The chemotherapeutically active pharmaceutical composition is independent of all personal characteristics of a subject such as age, height, weight, gender, and so forth. Also, the pharmaceutical composition may be used to treat subjects that do not respond to conventional methods of treatment and/or are ineligible for surgical resection and liver transplantation. Additionally, the seleno amino acid derivative compound targets multiple signalling pathways of the tumour and provides high anti-tumour efficacy. Further, the use of the seleno amino acid derivative compound is not limited to the treatment of malignant hepatic cells. Moreover, the at least one pharmaceutically acceptable seleno amino acid derivative compound has minimal side-effects and can be combined with other treatment methods to further prolong survival of the subject.

In one embodiment of the present disclosure, the term 'subject' used here in refers to a patient undergoing treatment of liver or pancreas malignancy.

In an embodiment, the term 'cell activity' used here in refers to the response or reaction of a cell exhibited towards the chemotherapeutically active pharmaceutical compound.

In an embodiment, the term 'beta-elimination activity' used herein is defined as the rate of the elimination or removal of a group from a β-carbon by the action of β-lyase enzyme, wherein β-carbon is defined as the carbon located adjacent to the carbon (α) on which the functional group is attached. The seleno amino acid derivative compound is typically selenocysteine, selenocystine, selenium-methyl-L-selenocysteine or a pharmaceutically acceptable salt or ester thereof. For example, selenium-methyl-L-selenocysteine (SMC) is an amino acid that is well tolerated in mammals. The compound is also sometimes referred to with the abbreviation MSC (methylselenocysteine).

In another embodiment, the cancer cells may exhibit higher cell activity than non-cancer cells. Therefore, the beta-elimination or transamination activity of the cancer cell may be inherently higher than non-cancer cells. In accordance, the seleno amino acid derivative compounds may inhibit the growth of cancer cells while non-cancer cells may be marginally affected at equivalent pharmaceutical dosages. This is also shown below in the Experimental part.

In an embodiment, the term 'excipient' used herein refers to an inactive substance that serves as a vehicle or a medium for delivering a drug or other active substance to a targeted organ. Indeed, according to an embodiment, the pharmaceutical composition comprises a pharmaceutically acceptable excipient. Specifically, the at least one excipient may be utilized for carrying the at least one pharmaceutically acceptable seleno amino acid derivative compound to the organ.

As mentioned above, use of synthetic L-Se-methylselenocystein as a nutraceutical for preventing or reducing the risk of developing liver cancer is known in the art. However, what is not known but what instead is both novel and non-obvious for a person skilled in the art at the time of filing this application, is that normal hepatocytes are far more resistant to seleno amino acid derivative compounds than malignant hepatocytes. There is indeed a significant difference in the sensitivity of normal hepatocytes and hepatocellular carcinoma cell (HCC) lines. Overexpression of KYAT1 results in increased sensitivity and thereby decreased IC50 of SMC.

Indeed, as is shown below, IC50 of the malignant hepatocytes is 18% when compared to normal hepatocytes (IC50 is the concentration of an inhibitor where the response (or binding) is reduced by half, as is known to a person skilled in the art). Furthermore, and as is again shown below, modulating substances affect the sensitivity of the malignant hepatocytes, thus leading to a synergistic effect according to one embodiment. Still further, it is possible to use mutant KYAT1 enzymes which lead to a marked increase in the cytotoxicity of the seleno amino acid derivative compounds. Another option to increase the cytotoxicity of the seleno amino acid derivative compounds is to use them together with natural alfa-keto derivative phenyl pyruvic acid, according to an embodiment.

Indeed, the SMC (also called MSC as explained above) has an increased cytotoxicity in tumour cells compared to normal cells. This effect is observed especially in the case of liver and pancreas cancers. The SMC can be used in connection with different components. The intracellular beta-elimination activity of kynurenine aminotransferase I (KYAT1) (UniProtKB—Q16773-1) (SEQ ID NO:1) or kynurenine aminotransferase III (KYAT3) (UniProtKB—Q6YP21-1) enzyme leads to significantly increased cytotoxicity of the SMC. The present pharmaceutical composition thus has a beta-elimination activity dependent tumor specificity.

According to an embodiment, the pharmaceutical composition further comprises an agent capable of increasing cytotoxicity of the seleno amino acid derivative compound. It may thus comprise one or several compounds modulating SMC metabolizing enzymes. According to another embodiment, said agent is selected from a group consisting of: indole pyruvic acid (IPA), phenyl pyruvic acid (PPA), α-keto-γ-methylthiobutyrate (KMB), dimethyl-2-oxoglutarate (aKG), L-phenylalanine, pyridoxal 5'-phosphate (PLP) hydrate, L-tryptophan, homoserine (HS), DL-propargylglycine (PAG), 2-amino-2-methyl-1,3-propanediol, N-N-dimethyl formamide and 3-indoleacetic acid (IAA). These agents could also be administered separately from the other agents, i.e. as part of a dosage regime. The administration route could be oral, intravenous or intramuscular.

Indeed, the degree of beta-elimination or transamination can be controlled by these substances. IPA, αKG, KMB, PPA and PLP increase the cytotoxicity of SMC which is more prominent when used together with overexpression of KYAT1 (i.e. the mutant protein, see below). These substances inhibit transamination and favor beta-elimination. Even without the presence of mutated KYATI, IPA has been found to increase the cytotoxicity of SMC.

The cytotoxicity of SMC can also be increased by site-directed mutagenesis of KYAT1. Such KYAT1 mutants can be used alone or in combination with one of the compounds listed above. The combination of overexpression of mutant KYAT1 (Y101HKYAT1 and H279FKYAT1) with PPA results in a very significant increase in sensitivity of HCC cells to SMC.

Thus, according to yet another embodiment, the pharmaceutical composition further comprises mutant kynurenine aminotransferase I enzyme or mutant kynurenine aminotransferase III enzyme having increased beta-elimination activity. Alternatively, it is possible to use nucleic acid sequences coding for these proteins.

Such mutant proteins or nucleic acid sequences can also be administered separately, either at the same time as the present pharmaceutical composition, or separately. They can for example be administered encapsulated, in any route, e.g. per oral, intravenously or intramuscularly.

For example, the nucleic acid may be controlled by the addition of microRNA switches regulating the expression of the nucleic acid such that it is down-regulated in normal tissue relative to tumorous tissue within the target organ (see e.g. Jain et al. (2018) Nucleic Acid Therapeutics Vol 28 No. 5: published online). The nucleic acid can be delivered in various ways. For example, the nucleic acid may be delivered as a modified RNA encapsulated in a nanoparticle formulation trophic for the target organ and/or tumor (see e.g. Jain et al. (2018) Nucleic Acid Therapeutics Vol 28 No. 5: published online). Alternatively, the nucleic acid may be delivered as an mRNA encapsulated within an exosome trophic for the target organ and/or tumor (see e.g. Liang et al. (2018) Int J Nanomedicine; Pomatta et al. (2019) Mol Ther Methods Clin December 13:133; Sutaira et al. (2017) Pharm Res 34:1053). As a further alternative, the nucleic acid may be delivered via a viral construct trophic for the target organ (see e.g. Kattenhorn (2016) Human Gene Ther 27:947).

Mutant proteins can be delivered by any suitable method. Such methods have e.g. been described in Kasuya et al. (2008) J Biosci Bioeng 106:99 and Yu et al. (2005) FEBS J. 272:3651).

Such a treatment in combination with SMC with or without alfa-ketoacid analogues (see above) may be highly cytotoxic to malignant cells. Two such mutants have been developed, and are named H279F (i.e. a histidine (His or H) to phenylalanine (Phe or F) substitution at position 279) and Y101H (i.e. a tyrosine (Tyr or Y) to histidine (His or H) substitution at position 101. It is believed that it is possible to develop further mutant forms of KYAT1 that show increased beta-elimination activity contributing to an increased cytotoxicity of SMC. Such development is within the normal practice of a person skilled in the art, now that it is known that such effect is obtainable. Similarly, such mutant proteins can also be developed for KYAT3. It is believed that SMC has not previously been shown to be efficient in the treatment of liver cancer and pancreas cancer. The use of SMC for these malignancies is thus novel and shows a significant potential for treatment of these cancers. In addition, the activity of KYAT1 may be altered by natural and/or synthetic substances. It is also believed that this has not been previously shown in the context of SMC. Especially PPA, IPA and KMB (see above) efficiently modulate the activity of KYAT1 and make the SMC even more cytotoxic. Furthermore, the concept of site-directed mutagenesis on KYAT1 is also believed to be novel. To alter the enzyme activity by site-directed mutagenesis where single amino acids are exchanged is new and non-obvious in the context of increased cytotoxicity for SMC. The mutagenesis concept in combination with the modifying substances is also believed to be novel and it is also very interesting in the medical sense, as it is believed to have a great potential in a therapeutic context.

In an embodiment, the organ may be liver, but the present description is not limited to liver. Specifically, the cancer cells of the liver may include malignant hepatic cell, cholangiocytes, stellate cells and so forth. Accordingly, the chemotherapeutically active pharmaceutical composition may be effective against hepatocellular carcinoma, cholangiocarcinoma, angiocarcinoma and so forth.

In one embodiment, the pharmaceutically acceptable seleno amino acid derivative compound may include pharmaceutically acceptable salts of the seleno amino acid derivative compound and esters thereof. According to this embodiment, selenium amount in the at least one pharmaceutically acceptable seleno amino acid derivative compound may range between 80-1200 micrograms.

In another embodiment, the at least one pharmaceutically seleno amino acid derivative compound may be selenium-methyl-L-selenocysteine (SMC) or a pharmaceutically acceptable salt or ester thereof.

SMC is a monomethylated seleno-amino acid in which selenium replaces the sulphur of the S-methylcysteine molecule. Structure of the SMC presented as follows:

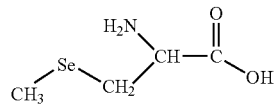

In an embodiment, an effective amount of selenium-methyl-L-selenocysteine may range between 100-4400 micrograms per day. The amount of selenium-methyl-L-selenocysteine may range for example from 100, 200, 300, 350, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000 or 4100 micrograms per day up to 300, 350, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300 or 4400 micrograms per day. The absorption of the seleno amino acid derivative compound SMC is highly efficient as it is capable of inducing synthesis of selenium transport protein SELENOP in HepG2 cells.

In an embodiment, the tissue-specific relative abundance of cysteine transporters in the apical side of cell membrane determines the relative distribution of the seleno amino acid derivative compound in the tissue of the patient.

In an embodiment, the at least one excipient may include but not limited to disintegrator, binder, filler, sweetener, flavouring agent, molecule carrier, and coating agent.

In an exemplary embodiment, the excipient used herein may be methyl cellulose. Further, in this embodiment concentration of the methyl cellulose may range between 75-95%.

In an embodiment, a dose of the chemotherapeutically active pharmaceutical composition comprises at least one of: a single dose, multiple uniform dosages, discrete dosages. In such embodiment, the multiple uniform dosages and the discrete dosages are per day dosages, separated by a time interval. In one embodiment, the dose of SMC/MSC may be a single per day dose. In another embodiment, the dose of SMC/MSC may be multiple, uniform dosages separated by a time interval. For instance, the SMC/MSC dosages may be four dosages of 100 micrograms SMC/MSC separated by the time interval of 6 hours between two consecutive dosages and resulting in the multiple, uniform dose of 400 micrograms per day.

In yet another embodiment, the dose of SMC/MSC may be discrete dosages separated by a time interval. For example, the calculated SMC/MSC dosages are three discrete dosages of 100 micrograms, 150 micrograms, and 150 micrograms separated by the time interval of 6 hours between two consecutive dosages and resulting in the discrete per day dose of 400 micrograms SMC/MSC.

In an exemplary embodiment, for the subject a maximum tolerated dose (MTD) of SMC may range between 400-2400 micrograms per day based upon personal characteristics and dose-limiting toxicity (DLT) of the subject. The term "maximum tolerated dose" (MTD) used herein refers to a highest dose level of SMC at which none of the subject experiences DLT.

In one embodiment, an effective amount of selenium-methyl-L-selenocysteine may range between 200-2400 micrograms per day. For example, the effective amount of SMC may include but not limited to 400 micrograms per day, 800 micrograms per day, 1200 micrograms per day, 1600 micrograms per day, 2000 micrograms per day, and 2400 micrograms per day.

In an embodiment, the chemotherapeutically active pharmaceutical composition is in an orally administrable form. In another embodiment, the pharmaceutical composition containing the effective amount of SMC may be one of: an instant release formulation, a sustained release formulation, a controlled release formulation.

The present disclosure provides a method for treating liver or pancreas cancer, comprising administration of:
a) a chemotherapeutically active pharmaceutical composition comprising at least one pharmaceutically acceptable seleno amino acid derivative compound, and
b) an agent capable of increasing cytotoxicity of the seleno amino acid derivative compound.

The method includes orally administering to a subject an effective amount of the above-defined pharmaceutical composition in per day doses. The embodiments and variations given above apply to the method mutatis mutandis.

In another embodiment, the present disclosure may provide a method for determining a dose of a chemotherapeutically active pharmaceutical composition for inhibiting growth of cancer cells, including steps of: measuring cell activity of the cancer cell, wherein the cell activity comprises at least one of a beta-elimination activity, and a transamination activity; comparing cell activity of the cancer cell to a predefined threshold cell activity; and calculating the dose of the chemotherapeutically active pharmaceutical composition based on the compared cell activity.

In an embodiment, the beta-elimination activity includes cleaving selenium-methyl-L-selenocysteine to its active form monomethylselenol by beta-lyase, which is an aminotransferase in presence of the β-lyase enzyme. The active form, monomethylselenol remains more bio-available for anticancer effects as compared to the other forms of the SMC. The monomethylselenol can further be de-methylated into hydrogen selenide and incorporated into selenocysteine in selenoprotein biosynthetic pathway.

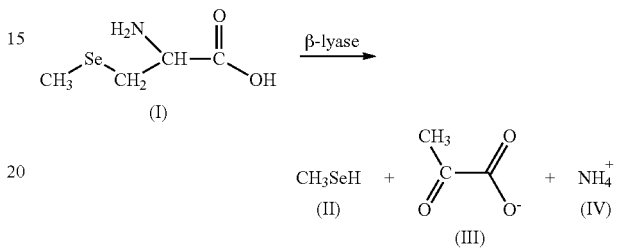

wherein
(I) is selenium-methyl-L-selenocysteine
(II) is monomethylselenol
(III) is pyruvate
(IV) is ammonia In another embodiment, measuring the cell activity also includes measuring a transamination activity of cancer cell of the subject. The term "transamination activity" used herein is defined as the rate of chemical reaction involving transfer of an amino group to a keto-acid to form new amino acids.

In yet another embodiment, the method further includes comparing cell activity of the cancer cell to a predefined threshold cell activity.

In an embodiment, the term "predefined threshold cell activity" used herein is defined as the response or reaction exhibited by a healthy (non-cancer) cell of the subject towards the chemotherapeutically active pharmaceutical compound. The predefined threshold cell activity of the subject may vary depending upon the age, height, weight, gender, pre-existing conditions of the subject, and so forth. In an embodiment, the method also comprises calculating the dose of the chemotherapeutically active pharmaceutical composition based on the compared cell activity.

In one embodiment, the cancer cell is a hepatic cell. The hepatic cells also known as perisinusoidal cells or Ito cells (earlier lipocytes or fat-storing cells), are pericytes found in the perisinusoidal space of the liver, also known as the space of Disse (a small area between the sinusoids and hepatocytes).

In one embodiment, the calculated dose of SMC may be multiple, uniform dosages separated by a time interval. For instance, the calculated SMC dosages may be four dosages of 200 micrograms SMC separated by the time interval of 6 hours between two consecutive dosages and resulting in the multiple, uniform dose of 400 micrograms per day.

In another embodiment, the calculated dose of SMC may be discrete dosages separated by a time interval. For example, the calculated SMC dosages are three discrete dosages of 200 micrograms, 250 micrograms, and 250 micrograms separated by the time interval of 6 hours between two consecutive dosages and resulting in the discrete per day dose of 400 micrograms SMC. In another exemplary embodiment, for the subject a maximum tolerated dose (MTD) of SMC may range between 400-2400 micrograms per day based upon personal characteristics and DLT of the subject.

In an embodiment, the chemotherapeutically active pharmaceutical composition containing seleno amino acid derivative compound may be used as second line treatment for inhibiting growth of cancer cells of the liver or pancreas. In this embodiment, the second line treatment may include but not limited to post-surgical and/or post transplantation treatment.

In yet another embodiment, the chemotherapeutically active pharmaceutical composition containing seleno amino acid derivative compound may be used in combination with sorafenib or any cytostatic drug for inhibiting growth of cancer cells of the liver or pancreas.

In a further aspect, the disclosed embodiment relates to a mutant kynurenine aminotransferase I or III protein having increased beta-elimination activity or a nucleic acid sequence coding for such a mutant protein. In one embodiment, the mutant kynurenine aminotransferase I comprises or consists of the sequence set forth in SEQ ID NO:2 or SEQ ID NO:3.

In addition, the disclosed embodiment relates to the embodiments:

Embodiment 1. A chemotherapeutically active pharmaceutical composition for treating carcinogenic cells of an organ, the pharmaceutical composition comprising at least one pharmaceutically acceptable seleno amino acid derivative compound, wherein the intracellular beta-elimination activity of the kynurenine aminotransferase I or kynurenine aminotransferase III enzyme of the carcinogenic cell is at least 1.5 times higher than the intracellular beta-elimination activity of the kynurenine aminotransferase I or kynurenine aminotransferase III enzyme of a non-carcinogenic cell of the organ, and wherein the organ is liver or pancreas.

Embodiment 2. A pharmaceutical composition according to embodiment 1, wherein the seleno amino acid derivative compound is selenocysteine, selenocystine, selenium-methyl-L-selenocysteine or a pharmaceutically acceptable salt or ester thereof.

Embodiment 3. A pharmaceutical composition according to embodiment 1 or 2, wherein selenium concentration in the at least one pharmaceutically acceptable seleno amino acid derivative compound ranges between 80-1200 micrograms.

Embodiment 4. A pharmaceutical composition according to embodiment 2, wherein an effective amount of selenium-methyl-L-selenocysteine ranges between 200-2400 micrograms per day.

Embodiment 5. A pharmaceutical composition according to any one of the preceding embodiments, further comprising an agent capable of increasing cytotoxicity of the seleno amino acid derivative compound.

Embodiment 6. A pharmaceutical composition according to embodiment 5, wherein the agent is selected from a group consisting of amino oxyacetic acid, indole pyruvic acid, phenyl pyruvic acid, α-keto-γ-methylthiobutyrate, dimethyl-2-oxoglutarate, L-phenylalanine, pyridoxal 5'-phosphate hydrate, L-tryptophan, homoserine, DL-propargylglycine, 2-amino-2-methyl-1,3-propanediol, N-N-dimethyl formamide and 3-indoleacetic acid.

Embodiment 7. A pharmaceutical composition according to any one of the preceding embodiments, further comprising the mutant proteins to increase the beta-elimination activity the mutant kynurenine aminotransferase I or III enzyme.

Embodiment 8. A pharmaceutical composition according to any of the preceding embodiments, wherein the chemotherapeutically active pharmaceutical composition is one of an instant release formulation, a sustained release formulation, a controlled release formulation.

Embodiment 9. A pharmaceutical composition according to any of the preceding embodiments, wherein the chemotherapeutically active pharmaceutical composition is in an orally, intramuscularly or intravenously administrable form.

Embodiment 10. A pharmaceutical composition according to any of the preceding embodiments, wherein a dose of the chemotherapeutically active pharmaceutical composition comprises at least one of a single dose, multiple uniform dosages, discrete dosages.

Embodiment 11. A pharmaceutical composition according to embodiment 10, wherein the multiple uniform dosages and the discrete dosages are per day dosages, separated by a time interval.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

EXPERIMENTAL PART

The present disclosure was tested in vitro by comparing the effect of the various components of the pharmaceutically active composition on normal hepatocytes and malignant hepatocytes (HCC).

Example 1

Normal hepatocytes and malignant hepatocytes (HCC) were incubated in the presence of various concentrations of SMC. After 72 h, the ATP content of lysed cells, which is proportional to the number of viable cells, was measured using a luminescence-based CellTiter Glo Kit (Promega) according to manufacturer's protocol using a FLx100 Luminometer (BioTek).

Table 1 below shows the IC50 of SMC in HCC relative to normal hepatocytes. The results show that tumour cells are far more sensitive to SMC compared to normal cells.

TABLE 1

| Cells | SMC IC50 (percentage of control) |
| --- | --- |
| Normal hepatocytes | 100 |
| Hepatocellular carcinoma | 18 |

Example 2

Another test was with induction of wild type and mutant KYAT1 (human kynurenine aminotransferase I (UniProtKB-Q16773-1)) in liver tumour cells.

KYAT1 belongs to the type I aminotransferase (AT) enzyme family. The prototypic enzyme for this family is the aspartate aminotransferase (AAT) which is well studied. AT uses the vitamin B6 derivative PLP to perform the enzymatic reaction. All ATs display also beta-elimination activity in addition to transamination. The first steps in these two processes leading to the formation of the quinonic form of the external aldimine are identical. External aldimine is a branching point and the process can go into transamination, beta-elimination or racemation paths.

The crystal structure of human KYAT1 has been determined for several complexes. The complex of KYAT1 with the cofactor PLP and the inhibitor L-Phe was used to create molecular models of Seleno-methyl Cystein (SMC) in complex with KYAT1 (FIG. 1). Our approach has been to identify residues that can be mutated in order to enhance beta-elimination of SMC, resulting in increased selenol production. This can be done by changing the substrate specificity of KYAT1 from kynurenine to SMC, or by changing kinetics of reprotonation of Calpha in the substrate. Several residues were mutated to check their potential involvement into the selenol formation. Mutations of Tyr 101 to His (Y101H) and His279 to Phe (H279F) resulted in higher selenol production by KYAT1 using SMC as a substrate.

HEPG2 cells were transfected with pEGFP-N1 (Clontech)-based expression vectors in which wild type or mutant KYAT1 coding sequences had been cloned. The mutants tested (Y101H (SEQ ID NO:2) and H279F (SEQ ID NO:3)) had been selected based on in silico molecular modelling of the binding of MSC to the enzyme. Viability was determined after 72 h as described in Example 1.

The results, relative to HEPG2 cells transfected with a control vector, are shown in Table 2. Transfection with wild type KYAT1 already reduced the IC50 significantly, but the mutant KYAT1's were significantly more effective, indicating that higher beta elimination activity causes considerably higher cytotoxicity.

TABLE 2

| Cells | SMC IC50 (percentage of control) |
|---|---|
| Wild type KYAT1 | 40 |
| H279FKYAT1 | 17 |
| Y101HKYAT1 | 5 |

Example 3

The effect of wild type and mutant KYAT1 in HEPG2 liver tumour cells in the presence of PPA (phenyl pyruvic acid) was also tested. The final concentration of PPA (phenyl pyruvic acid) was 0.4 mM. Viability was determined after 72 h as described in Example 1.

The results, relative to HEPG2 cells transfected with a control vector, are shown in Table 3. The mutant KYAT1's were more effective with significantly higher beta-elimination activity causing considerably higher cytotoxicity. The presence of PPA leads to a further decrease in the IC50s, showing the importance of beta-elimination activity. The cytotoxicity of MSC in cells in which the Y101HKYAT1 was induced was significantly enhanced.

TABLE 3

| Cells | SMC IC50 (percentage of control) |
|---|---|
| Wild type KTKYAT1 | 22 |
| H279FKYAT1 | 10 |
| Y101HKYAT1 | 2 |

Example 4

Additionally, the effects of the presence of other alfaketoacid analogues on HCC cell viability were tested according to the procedure described in Example 1.

The results are shown in Tables 4 (relative to PPA treated HCC cells) and 5 (relative to untreated KYAT induced cells) here below. Indole pyruvic acid (IPA) has an even stronger effect on the cytotoxicity compared to PPA.

TABLE 4

| Native HCC cells | SMC IC50 (percentage of control) |
|---|---|
| PPA (phenyl pyruvic acid) | 100 |
| IPA (indole pyruvic acid) | 38 |

TABLE 5

| KYAT induced cells | SMC IS50 (percentage of control) |
|---|---|
| PPA (phenyl pyruvic acid) | 38 |
| IPA (indole pyruvic acid) | 35 |

SEQUENCE LISTING

SEQ ID NO:1 (human KYAT1)
MAKQLQARRL DGIDYNPWVE FVKLASEHDV VNLGQGFPDF PPPDFAVEAF QHAVSGDFML
NQYTKTFGYP PLTKILASFF GELLGQEIDP LRNVLVTVGG YGALFTAFQA LVDEGDEVII
IEPFFDCYEP MTMMAGGRPV FVSLKPGPIQ NGELGSSSNW QLDPMELAGK FTSRTKALVL
NTPNNPLGKV FSREELELVA SLCQQHDVVC ITDEVYQWMV YDGHQHISIA SLPGMWERTL
TIGSAGKTFS ATGWKVGWVL GPDHIMKHLR TVHQNSVFHC PTQSQAAVAE SFEREQLLFR
QPSSYFVQFP QAMQRCRDHM IRSLQSVGLK PIIPQGSYFL ITDISDFKRK MPDLPGAVDE
PYDRRFVKWM IKNKGLVAIP VSIFYSVPHQ KHFDHYIRFC FVKDEATLQA MDEKLRKWKV
EL SEQ ID NO:2 (Y101H mutant)
MAKQLQARRL DGIDYNPWVE FVKLASEHDV VNLGQGFPDF PPPDFAVEAF QHAVSGDFML
NQYTKTFGYP PLTKILASFF GELLGQEIDP LRNVLVTVGG HGALFTAFQA LVDEGDEVII
IEPFFDCYEP MTMMAGGRPV FVSLKPGPIQ NGELGSSSNW QLDPMELAGK FTSRTKALVL
NTPNNPLGKV FSREELELVA SLCQQHDVVC ITDEVYQWMV YDGHQHISIA SLPGMWERTL
TIGSAGKTFS ATGWKVGWVL GPDHIMKHLR TVHQNSVFHC PTQSQAAVAE SFEREQLLFR QPSSYFVQFP QAMQRCRDHM IRSLQSVGLK PIIPQGSYFL ITDISDFKRK MPDLPGAVDE PYDRRFVKWM IKNKGLVAIP VSIFYSVPHQ KHFDHYIRFC FVKDEATLQA MDEKLRKWKV EL SEQ ID NO: 3 (H279F mutant)
MAKQLQARRL DGIDYNPWVE FVKLASEHDV VNLGQGFPDF PPPDFAVEAF QHAVSGDFML NQYTKTFGYP PLTKILASFF GELLGQEIDP LRNVLVTVGG YGALFTAFQA LVDEGDEVII IEPFFDCYEP MTMMAGGRPV FVSLKPGPIQ NGELGSSSNW QLDPMELAGK FTSRTKALVL NTPNNPLGKV FSREELELVA SLCQQHDVVC ITDEVYQWMV YDGHQHISIA SLPGMWERTL TIGSAGKTFS ATGWKVGWVL GPDHIMKHLR TVHQNSVFFC PTQSQAAVAE SFEREQLLFR QPSSYFVQFP QAMQRCRDHM IRSLQSVGLK PIIPQGSYFL ITDISDFKRK MPDLPGAVDE PYDRRFVKWM IKNKGLVAIP VSIFYSVPHQ KHFDHYIRFC FVKDEATLQA MDEKLRKWKV EL

---

The invention claimed is:

1. A chemotherapeutically active pharmaceutical composition comprising at least one pharmaceutically acceptable seleno amino acid derivative compound for use in the treatment of liver or pancreas cancer, the pharmaceutically acceptable seleno amino acid derivative compound including selenocysteine, selenocystine, selenium-methyl-L-selenocysteine or a pharmaceutically acceptable salt or ester thereof, wherein said chemotherapeutically active pharmaceutical composition is used in combination with an agent capable of increasing cytotoxicity of the pharmaceutically acceptable seleno amino acid derivative compound, the agent capable of increasing cytotoxicity of the pharmaceutically acceptable seleno amino acid derivative compound is selected from the group consisting of: α-keto-γ-methylthiobutyrate, dimethyl-2-oxoglutarate, pyridoxal 5'-phosphate hydrate, homoserine, DL-propargylglycine, 2-amino-2-methyl-1,3-propanediol, N-N-dimethyl formamide, 3-indoleacetic acid, a mutant kynurenine aminotransferase I protein having a Tyr to His substitution at position 101 or a His to Phe substitution at position 279, a nucleic acid sequence coding for the mutant kynurenine aminotransferase I protein and mixtures thereof.

2. A chemotherapeutically active pharmaceutical composition for use according to claim 1, wherein selenium amount in the at least one pharmaceutically acceptable seleno amino acid derivative compound ranges between 80-1200 micrograms.

3. A chemotherapeutically active pharmaceutical composition for use according to claim 1, wherein the seleno amino acid derivative is selenium-methyl-L-selenocysteine and wherein selenium-methyl-L-selenocysteine is dosed between 200-2400 micrograms per day.

4. A chemotherapeutically active pharmaceutical composition for use according to claim 1, wherein said agent capable of increasing cytotoxicity of the seleno amino acid derivative compound is a mutant kynurenine aminotransferase I or III proteins having increased beta-elimination activity or a nucleic acid sequence coding for such a mutant protein.

5. A chemotherapeutically active pharmaceutical composition for use according to claim 4, wherein said agent capable of increasing cytotoxicity of the seleno amino acid derivative compound is a mutant kynurenine aminotransferase I protein having a Tyr to His substitution at position 101 or a His to Phe substitution at position 279.

6. A chemotherapeutically active pharmaceutical composition for use according to claim 1, wherein said agent capable of increasing cytotoxicity of the seleno amino acid derivative compound is administered separately.

7. A chemotherapeutically active pharmaceutical composition for use according to claim 1, wherein said chemotherapeutically active pharmaceutical composition is used in combination with
   a) indole pyruvic acid or phenyl pyruvic acid, and
   b) a mutant kynurenine aminotransferase I protein having a Tyr to His substitution at position 101 or a His to Phe substitution at position 279, or a nucleic acid sequence coding for such a mutant kynurenine aminotransferase I protein.

8. A chemotherapeutically active pharmaceutical composition for use according to claim 4, wherein the nucleic acid is controlled by the addition of microRNA switches regulating the expression of the nucleic acid such that it is down-regulated in normal tissue relative to tumorous tissue within the target organ.

9. A chemotherapeutically active pharmaceutical composition for use according to claim 4, wherein the nucleic acid is delivered as a modified RNA encapsulated in a nanoparticle formulation trophic for the target organ and/or tumor.

10. A chemotherapeutically active pharmaceutical composition for use according to claim 4, wherein the nucleic acid is delivered as an mRNA encapsulated within an exosome trophic for the target organ and/or tumor.

11. A chemotherapeutically active pharmaceutical composition for use according to claim 4, wherein the nucleic acid is delivered via a viral construct trophic for the target organ.

12. A chemotherapeutically active pharmaceutical composition for use according to claim 1, wherein the chemotherapeutically active pharmaceutical composition is one of an instant release formulation, a sustained release formulation, a controlled release formulation.

13. A chemotherapeutically active pharmaceutical composition for use according to claim 1, wherein the chemotherapeutically active pharmaceutical composition is in an orally, intramuscularly or intravenously administrable form.

14. A chemotherapeutically active pharmaceutical composition for use according to claim 1, wherein the use of the chemotherapeutically active pharmaceutical composition comprises at least one of: a single dose, multiple uniform dosages, discrete dosages.

* * * * *